United States Patent [19]
Cordi et al.

[11] Patent Number: 5,677,325
[45] Date of Patent: Oct. 14, 1997

[54] 4-IMIDAZOLIDINONE COMPOUND

[75] Inventors: Alex Cordi, Suresnes; Jean-Michel Lacoste, Sevres; Mark Millan, Paris; Valérie Audinot, Croissy, all of France

[73] Assignee: Adir Et Compagnie, Courbevoie, France

[21] Appl. No.: 770,290

[22] Filed: Dec. 20, 1996

[30] Foreign Application Priority Data

Dec. 21, 1995 [FR] France .................................. 95 15223

[51] Int. Cl.$^6$ ...................... C07D 233/06; A61K 31/415
[52] U.S. Cl. ........................................ 514/386; 548/316.7
[58] Field of Search ........................... 514/386; 548/316.7

[56] References Cited

PUBLICATIONS

Harmon et al., Journal of Heterocyclic Chemistry, 7(2) 439–442 (1970).

*Primary Examiner*—Fiona T. Powers
*Attorney, Agent, or Firm*—The Firm of Gordon W. Hueschen

[57] ABSTRACT

Compound of formula (I):

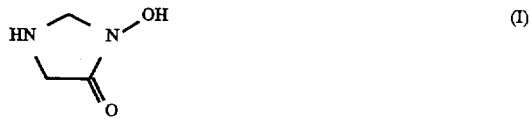

and its addition salts with a pharmaceutically acceptable acid or base, a medicinal products containing the same are useful as partial agonist of the glycine B site.

3 Claims, No Drawings

4-IMIDAZOLIDINONE COMPOUND

BACKGROUND OF THE INVENTION

The compound of the present invention, in addition to the fact that it is novel, is a powerful partial agonist of the glycine receptor site coupled to the N-methyl-D-aspartate (NMDA) receptor (glycine B receptor).

1. Field of the Invention

L-Glutamic acid and L-aspartic acid have the ability to activate the neurons of the central nervous system and many studies have demonstrated that these excitatory amino acids (EAA) correspond to the criteria defining a neurotransmitter. For this reason, the modulation of the neuronal events related to these EAAs appear to be an advantageous target in the treatment of neurological and psychiatric diseases.

Among the four groups of EAA receptors located post- and presynaptically, the NMDA receptor is associated with an ionic channel permeable to mono- and divalent cations (including calcium) but which is blocked by magnesium. The opening of the NMDA channel is regulated by a number of sites associated with the receptor and is in particular promoted by glycine, the effect of which is strychnine-insensitive. This glycine site is one of the major targets in modulating the activation of the NMDA receptor.

Positive modulation of NMDA transmission by acting as agonist at the glycine B receptors is a means for improving the functioning of learning and the memory in general (J. B. Monahan et al., Pharmacol. Biochem. & Behavior, 34, 649–653, 1989; W. E. Müller et al., Life Sciences, 55, No. 25/26, 2147/2153, 1994), as well as its dysfunctions related to the process of ageing, neurodegenerative diseases, dementias, such as Alzheimer's disease, Pick's disease, Huntington's chorea, schizophrenia or anxio-depressive conditions (A. Hashimoto et al., J. Neurochem., 60, No. 2, 783–786, 1993; P. Saransaari, Mechanisms of Ageing and Devel., 72, 57–66, 1993). Moreover, an agonist or partial agonist activity of the glycine B type could be useful in the treatment of convulsions, for example those associated with epilepsy (M. G. Baxter et al., CNS Drug Reviews, 1, No. 1, 74–90, 1995; D. O. Norris et al., Pharmacol. Biochem. & Behavior, 43, 609–612, 1992), in the treatment of pain (A. H. Dickenson et al., Neuroscience Lett., 121, 263–266, 1991; M. J. Millan et al., Europ. J. Pharmacol., 238, 445–447, 1993), in the control of the productive and deficient symptoms of schizophrenia (M. Ishimaru et al., Biol. Psychiatry, 35, 84–95, 1994; A. O. Sherman et al., Biol. Psychiatry, 30, 1191–1198, 1991), in the treatment of anxiety (R. Trullas et al., Europ. J. Pharmacol., 203, 379–385, 1991; J. T. Winslow et al., Europ. J. Pharmacol., 190, 11–21, 1990) and of depression (I. A. Paul et al., Psychopharm., 106, 285–287, 1992; R. Trullas cited above) and in the treatment of problems associated with the abuse of drugs such as alcohol (C. R. Breese et al., Brain Research, 674, 82–90, 1995; S. J. Deutsch et al., Clinical. Neuropharmacol., 12, No. 6, 483–489, 1989) and psychostimulants (G. E. Evoniuk et al., Psychopharm., 105, 125–128, 1991; E. Toth et al., Neurochem. Research, 11, No. 3, 393–400, 1986).

2. Prior Art Description

Simple 4-imidazolidinone derivatives have rarely been described in the literature. Nevertheless, mention may be made of the compounds described by R. E. Harmon et al. (J. Het. Chem., 70, Vol. 7 (2), p. 439–442).

No specific pharmacological activity has been described for these compounds in the prior art.

DETAILED DESCRIPTION OF THE INVENTION

More specifically, the present invention relates to 3-hydroxy-4-imidazolidinone of formula (I):

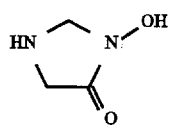

and to its addition salts with a pharmaceutically acceptable acid or base.

Mention may be made, among pharmaceutically acceptable acids, as non-limiting example, of hydrochloric, hydrobromic, sulfuric, phosphoric, acetic, trifluoroacetic, lactic, pyruvic, malonic, succinic, glutaric, fumaric, tartaric, maleic, citric, ascorbic, oxalic, methanesulfonic and camphoric acids and the like.

Mention may be made, among pharmaceutically acceptable bases, as non-limiting example, of sodium hydroxide, potassium hydroxide, triethylamine, tert-butylamine and the like.

The present invention also relates to the process for the preparation of this compound, characterized in that glycine-hydroxamic acid of formula (II):

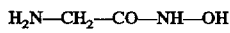

is reacted with an aqueous formaldehyde solution, to result in the compound of formula (I), which is purified, if appropriate, according to a conventional purification technique and which is converted, if desired, into its addition salts with a pharmaceutically acceptable acid or base.

Another subject of the present invention is the pharmaceutical compositions containing the compound of formula (I) as active principle, alone or in combination with one or a number of non-toxic, inert excipients or vehicles.

Mention may more particularly be made, among the pharmaceutical compositions according to the invention, of those which are suitable for oral, parenteral or nasal administration, simple or sugar-coated tablets, sublingual tablets, gelatin capsules, lozenges, suppositories or creams, ointments, dermal gels, and the like.

The useful dose varies according to the age and the weight of the patient, the nature and severity of the condition and the administration route. The latter can be oral, nasal, rectal or parenteral. Generally, the unit dose ranges between 1 and 1000 mg for a treatment taken 1 to 3 times per 24 hours.

The following examples illustrate the invention and do not limit it in any way.

The structure of the compound of the invention has been confirmed by the usual spectroscopic techniques (nuclear magnetic resonance, infrared, mass spectrometry, X-ray diffraction, and the like).

EXAMPLE 1

3-Hydroxy-4-imidazolidinone 0.9 ml of a 40% aqueous formaldehyde solution is added, in one step, at 20° C. to a solution, maintained under a nitrogen atmosphere, containing 11 mmol of glycinehydroxamic acid in 50 ml of ethanol. The mixture is then heated at reflux for 3 hours, then cooled to 20° C. and stirred at this temperature overnight. The crystalline residue obtained is filtered off and washed with ethanol and then with ethyl ether. The expected product is then purified by crystallization from ethanol.

Melting point: 147°–148° C.

| Elemental microanalysis: | | | |
|---|---|---|---|
| | C% | H% | N% |
| calculated | 35.29 | 5.92 | 27.44 |
| found | 35.21 | 5.72 | 27.08 |

Pharmacological Study of the Compound of the Invention

EXAMPLE 2

Experiments on the Binding of [$^3$H]-glycine and of [$^3$H]-MK 801 to Rat Brain Membranes Material and Methods Preparation of the membranes (according to Yoneda et al., J. Neurochem., 55, 1, 237–244, 1990)

The membranes are prepared and used in the same way for both radioligands. The buffers are prepared with sterile Milli-Q water (Millipore) which is deionized and filtered, just before use, on a nitrocellulose filter (0.45 μm).

After dissection, the brains from rats (Wistar males, 240–260 g), freed from the cerebellum, are placed in an ice-cold buffer comprising Tris-acetate (1 mM), EGTA (1 mM) and sucrose (320 mM) at pH 7. The brains are milled and then homogenized using a polytron. The suspension is centrifuged for 10 minutes at 1000 g and the supernatent containing the membranes is recovered and recentrifuged for 20 minutes at 35000 g. The pellet, freed from a brown ring, is recovered in a lysis buffer comprising Tris-acetate (1 mM) and EGTA (1 mM) at pH 8. The suspension is then left for 15 minutes at 4° C. and is then centrifuged for 20 minutes at 35000 g. The pellet is recovered in a Tris-acetate (50 mM) buffer at pH 7.4 containing 0.08% Triton and left for 30 minutes at 4° C.

After two successive centrifugings, the pellet is taken up in Tris-acetate (50 mM) buffer at pH 7.4, divided into aliquots and stored at −80° C. On the day of the experiment, at most 3 weeks after the preparation, the membranes are washed twice with Tris-acetate (50 mM) buffer at pH 7.4.

Binding experiments (according to Yoneda et al., J. Neurochem., 60, 2, 634–645, 1993)

| Site | Radioligand | Non-specific binding | Incubation |
|---|---|---|---|
| Glycine B | [$^3$H]-Glycine (10 nM) | Glycine (10 Mm) | 20 minutes at 4° C. |
| NMDA channel | [$^3$H]-MK 801 (1 nM) | PCP (10 μM) | 120 minutes at 20° C. |

The free and bound radioligands are separated on GF/B filters, preimpregnated with PEI (0.1%), using a Brandle filtration device. In both cases, filtration is carried out very quickly, using ice-cold Tris-acetate (50 mM) buffer at pH 7.4 (containing 10 mM of MgSO$_4$ for the experiments with [$^3$H]-glycine). Each filter is rinsed 3 times. The radioactivity is measured using a β-counter (Tricarb 1500, Packard) and expressed in dpm. The curves obtained are analyzed using GraphPad Prism software (non-linear regression).

Results (Table 1)

The binding to the glycine B site reflects the affinity (IC$_{50}$) of glycinergic products for this site. Glycine, an endogenous agonist ligand, the agonist D-serine, also surmised to be an endogenous agonist (A. Hashimoto et al., I. Neurochem., 60, No. 2, 783–786, 1993) and the antagonist L-701,324 respectively exhibit affinities of the order of 0.247 μM, 0.673 μM and 0.026 μM.

The compound of the invention exhibits an affinity similar to that of the partial agonist D-cycloserine and of the antagonist (+) HA 966, i.e. 6.8, 7.4 and 7.3 μM respectively.

The opening of the channel of the NMDA receptor complex is modulated positively by the glycinergic site. MK 801 is a ligand which acts by attaching itself within the channel. The binding of [$^3$H]-MK 801 is thus stimulated by a glycinergic agonist and inhibited by a glycinergic antagonist. Thus, like glycine, D-serine and D-cycloserine, the compound of the invention stimulates the binding of [$^3$H]-MK 801. It should be noted that, for the agonists, the EC$_{50}$ values obtained with respect to [$^3$H]-MK 801 binding are generally lower than the IC$_{50}$ values obtained with respect to [$^3$H]-glycine binding. Regarding the effectiveness, glycine exerts a maximum stimulating effect of 59%, an effect which is similar to that of D-serine, whereas D-cycloserine, a partial agonist, exerts an effect of only 22%. The compound of the invention behaves as an agonist, the effectiveness of which (46%) is markedly greater than that of D-cycloserine but slightly less than that of glycine and of D-serine. As regards the antagonists, the inhibiting effect obtained is virtually maximal.

TABLE 1

| | | [$^3$H]-Glycine | [$^3$H]-MK 801 | |
|---|---|---|---|---|
| | Product | IC$_{50}$ (μM) | EC$_{50}$ (μM) | ME (%) |
| | Compound of Example 1 | 6.812 ± 0.545 (7) | 4.330 ± 1731 (2) | +46 ± 3 at 10 μM |
| Agonists | Glycine | 0.247 ± 0.024 (19) | 0.068 ± 0.013 (4) | +59 ± 6 (4) at 10 μM |
| | D-Serine | 0.673 ± 0.198 (8) | 0.161 ± 83 (2) | +69 ± 20 (2) at 10 μM |
| Partial agonist | D-Cycloserine | 7.371 ± 1.748 (2) | 2.950 ± 683 (3) | +22 ± 9 at 100 μM |
| | | IC$_{50}$ (μM) | IC$_{50}$ (μM) | ME (%) |
| Antagonists | (+)-HA966 | 7.343 ± 1098 (4) | 6.729 (1) | −85 ± 7 (3) at 100 μM |
| | L 701,324 | 0.026 ± 0.007 (4) | 0.022 (1) | −91 ± 3 (2) at 1 μM |

IC$_{50}$: Concentration of the product necessary to inhibit the binding of the radioligand by 50%
EC$_{50}$: Concentration of the product necessary to stimulate the binding of the radioligand by 50%
ME: Maximum effect of the product obtained on the binding of [$^3$H]-MK 801 with respect to a base of 0%: + = stimulation and − = inhibition

EXAMPLE 3

Pharmaceutical Composition

| Formula for the preparation of 1000 tablets containing a dose of 10 mg | |
|---|---|
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

We claim:

1. A compound selected from that of formula (I):

and its addition salts with a pharmaceutically-acceptable acid or base.

2. A method for treating an animal or human living body afflicted with a condition requiring a partial agonist of the glycine B site comprising the step of administering to the living body an amount of a compound of claim 1 which is effective for alleviation of said condition.

3. A pharmaceutical composition useful as a glycine B partial agonist comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,677,325
DATED : October 14, 1997
INVENTOR(S) : Alex Cordi, Jean-Michel Lacoste, Mark Millan, Valerie Audinot It is certified that error appears in the above-indentified patent and that said Letters Patent is hereby corrected as shown below:

Column 4, line 22: "I. Neurochem., 60," should read -- J. Neurochem. 60, --.

Signed and Sealed this

Thirteenth Day of January, 1998

Attest:

BRUCE LEHMAN

Attesting Officer

Commissioner of Patents and Trademarks